US006743250B2

(12) United States Patent
Renfro

(10) Patent No.: US 6,743,250 B2
(45) Date of Patent: Jun. 1, 2004

(54) PORTABLE THERMAL RESCUE/RECOVERY SYSTEM

(76) Inventor: William Leonard Renfro, 1431 33$^{rd}$ St. NW., Washington, DC (US) 20007

( * ) Notice: Subject to any disclaimer, the term of this patent is extended or adjusted under 35 U.S.C. 154(b) by 0 days.

(21) Appl. No.: 10/084,228

(22) Filed: Feb. 28, 2002

(65) Prior Publication Data

US 2002/0193852 A1 Dec. 19, 2002

Related U.S. Application Data

(60) Provisional application No. 60/271,730, filed on Feb. 28, 2001.

(51) Int. Cl.$^7$ .............................. A61F 7/00; A61F 5/00; A61F 13/00
(52) U.S. Cl. ........................ 607/104; 607/108; 602/14; 128/847
(58) Field of Search .................. 607/96, 104, 108, 607/109, 110, 111; 602/2, 14; 604/289, 291, 310, 311; 128/847; 5/89.1, 413 AM, 421; 601/148, 149, 150, 151

(56) References Cited

U.S. PATENT DOCUMENTS

| | | | | |
|---|---|---|---|---|
| 4,353,359 A | * | 10/1982 | Milbauer | 601/166 |
| 4,747,408 A | * | 5/1988 | Chuan-Chih | 607/83 |
| 4,790,040 A | * | 12/1988 | Grilliot et al. | 5/413 R |
| 4,922,562 A | * | 5/1990 | Allred et al. | 5/627 |
| 5,067,921 A | * | 11/1991 | Bramham | 441/102 |
| 5,269,369 A | * | 12/1993 | Faghri | 607/104 |
| 5,516,233 A | | 5/1996 | Courtney | |
| 5,658,325 A | * | 8/1997 | Augustine | 607/107 |
| 5,669,088 A | * | 9/1997 | McNamee | 5/413 |
| 5,755,756 A | * | 5/1998 | Freedman et al. | 607/110 |
| 6,012,179 A | * | 1/2000 | Garrett et al. | 2/456 |
| 6,197,045 B1 | | 3/2001 | Carson | |
| 6,245,094 B1 | * | 6/2001 | Pompei | 607/104 |
| 6,277,144 B1 | | 8/2001 | Tomic-Edgar et al. | |
| 6,328,618 B1 | | 12/2001 | Fleischli | |

OTHER PUBLICATIONS

New Way Found To Prevent Stroke Damage, by Daniel Q. Haney, AP Medical Editor, Wednesday, Feb. 14, 2001; 11:56 a.m. EST (from Associated Press wire).
Sailing USA, http://www.sailingusa.info/sailing$_{13}$safety.htm (Found on the world wide web, no hard copy could be located).
Study Says Lowering Body Temperature Prevents Stroke Damage, by Daniel Q. Haney, AP Medical Editor, Wednesday, Feb. 14, 2001.

* cited by examiner

Primary Examiner—Linda C. M. Dvorak
Assistant Examiner—Kenneth G Schopfer

(57) ABSTRACT

A light weight, portable thermal rescue/recovery system for mammals up to 300 lbs. In weight, comprising of a mummy bag which contains a circulating liquid which is either heated when the mammal needs to be warmed as in the case of, for example, a mammal suffering from hypothermia, or cooled when the mammal's body temperature or skin temperature needs to be lowered as in the case of a burn, stroke and some heart attack victims. The mammal is placed into the mummy bag of the portable thermal rescue/recovery system which also has a pump to circulate the liquid and a heat exchanger to cool or heat the liquid. This portable thermal rescue/recovery system is suitable for all rescue vehicles including helicopters, boats, EMS ambulances, fire trucks, police cars, avalanche rescues, ice rescues and air cushion vehicles, as well as stretchers and other manual transport means, among others. The system has, in addition to means to control the temperature of the circulating liquid, means to add chemicals such as salt, oxygen, etc., and/or pharmaceuticals such as aloe, bacitracin, cortisone, topical circulatory stimulants, etc., and/or drugs such as antibiotics, nitroglycerin, pain killers, and other topical medications and/or medicines as indicated by the needs of the mammal.

11 Claims, 2 Drawing Sheets

PORTABLE THERMAL RESCUE/RECOVERY SYSTEM

This application is a utility patent application having benefit of Provisional Application Serial No. 60/271,730, filed on Feb. 28, 2001.

BACKGROUND OF THE INVENTION

1. Field of the Invention

The invention relates to portable thermal rescue systems designed to rapidly raise or rapidly lower and thereafter to control the body temperature of a mammal, particularly a human (or person) by thermal exchange between a liquid and the mammal via direct liquid-to-skin contact. The invention allows topical delivery of medicines to the mammal and is particularly apt for immediate treatment in the field of bum injuries, hypothermia, strokes, infarctions, heart attacks. Head injuries and other trauma where prompt temperature control a mammal's body is of therapeutic or medical value. The present invention generally relates to a water-proof mummy bag and related system for cooling and/or heating a mammal, particularly a human (or person) via thermal exchange with a liquid. The present invention is particularly apt for emergency, rapid treatment and also in situ emergency treatment for mammals suffering from hypothermia, exposure, strokes, heart attacks, infarctions, head injuries and other trauma.

2. Background Art

In medical emergencies where a mammal's body temperature is critical, techniques for raising or lowering a mammal's body temperature in a timely manner are limited by current technologies and means. The prior art, whether blankets, electric blankets, warming coats, hot water containers, heating pads or similar devices all transfer heat into a human (or other mammal) suffering hypothermia using an air medium and are limited by the low transfer rate of heat from air into the body through skin tissues. To increase heat transfer rates to an inanimate object, the temperature of the medium is simply increased. However, where the object is a mammal the temperature of the medium is limited to what the skin of the mammal can tolerate without bum damage. Since increasing the temperature of the air medium is limited, the rate of heat transfer is limited. Once the maximum tolerable air temperature has been reached increasing the rate of circulation of the air is the only way to increase the rate of transfer of heat to or from a mammal body. Sufficient air circulation is not practical or possible to reach the desired heat transfer rates. Since human skin (and most mammal skin) cannot tolerate the high temperatures of air that are required to achieve the heat transfer rates that are often required, it is often impossible to save the mammal's life. This result is due to the combination of three factors: first; the low heat capacity of medium of heat transfer—air, second, limitations on circulation of air and third, the low temperature tolerance for the skin of humans and mammals.

However, a liquid heat transfer medium such as water or other aqueous liquid uses the far more powerful heat transfer rates of conduction from liquid to the body of a mammal. This liquid-to-body heat transfer rate is four to five times that of the air-to-body heat transfer rate at the same temperature due in large part to the much higher heat capacity of aqueous liquids compared the heat capacity of air. As with air, circulating the liquid medium around the body increases the heat transfer rate.

Since both air and water heat transfer mechanisms operate through the skin, clothing inhibits the heat transfer from air and must be removed for optimal recovery of body temperature by air heat transfer. With a direct liquid heat transfer medium, removal of clothing, especially wet clothing, is not as critical, can be avoided and in bum cases, it is often is undesirable or impossible without harmful side effects. In these circumstances the mammal is placed directly in the liquid suspending the mammal, allowing the mammal's coverings or clothes to float free, rather than clinging to the body as in an attempted recovery of body temperature by air heat transfer. The far higher heat capacities and heat transfer rates of liquids combined with circulating the liquid makes this possible.

Human skin can easily tolerate without undesirable side effects, water temperatures of up to 110 degrees F. for extended periods of time as is frequently demonstrated by therapeutic and recreational users of hot tubs. For some mammals, higher temperatures may be tolerated. The ability of human and other mammal tissue to tolerate beyond a brief period, heat transfer rates from conduction due to temperature differences more than 12 degrees F. above normal body temperature, approximately 110 degrees F., is not known—and will not be until a mammal whose hypothermia is so extreme that their skin temperature is substantially below the normal 98.6 degrees F. and the thermal rescue system is put to work to save the mammal's life. Humans regularly wash and shower using water temperatures as high as 120 degrees F. In extreme hypothermia cases, a mammal's body temperature may be as low as 70 degrees F.—the minimum body temperature from which mammals frequently manage to recover from hypothermia. Some indication of local tolerances can come from frostbite recovery efforts, but a whole body experience is not known at this time.

Since the possible side effects for hypothermia mammals of heat transfer rates higher than those generated by 12-to 15 degree F. temperature differences have not yet been established, it is an important feature of the Portable Thermal Rescue/Recovery System that the temperature can be adjusted to the maximum ability and condition of each particular mammal to handle the rate of recovery.

In lowering body temperature, the bodies of mammals are able to withstand heat transfer rates resulting from immersion in liquids 40–50 degrees F. colder than normal body temperature. Since the body temperature of a mammal suffering from a trauma needing reduced body temperature need be lowered only 10 degrees F. to realize the therapeutic benefits, the liquid medium may not have to be cooled below ambient room temperatures of 70–75 degrees F. Where additional or more rapid cooling is needed, the circulation of the liquid by the pump can be added, increased or the water replaced.

BROAD DESCRIPTION OF THE INVENTION

When a mammal is suffering from hypothermia, whether from a marine accident or MOB (man overboard) incident ice collapse, circulatory infarction or other medical emergency or event causing exposure to the elements, the best first aid is to restore the body temperature of the mammal as quickly as possible without inducing secondary effects.

When a mammal has been burned, the best first aid is to place the burned areas in cool preferably oxygenated water as soon as possible. This cool water reduces scarring and further damage caused by the effect of excessive heat on human and animal tissues. Reducing the temperature by immersion in cool water has these benefits: first, it slows or stops continuing bum damage; second, it reduces the need of the skin tissue for oxygen; and third, it provides a source of supplemental oxygen to the burned tissues.

Where the area of the burn is large or covers a significant portion of the body so that local topical temperature relief of an ice-pack or a series of ice packs is not practical, possible or available, a thermal rescue/recovery system provides the best quickest means of providing first aid to both alleviate pain and limit further damage. In addition immersion in the liquid of the thermal rescue/recovery system promotes healing by eliminating or minimizing the need for damaged portions of the skin to support the weight of the mammal allowing all surface areas of the mammal to receive relief at the same time. This is especially valuable where burns cover sufficiently large portions of the body that some burned tissue has to support the weight of the body.

Medical research shows strokes typically occur when a blood clot lodges in the tree of arteries in the head, choking off the flow of blood. Quickly giving a clot dissolver can forestall much of the damage, but most mammals do not receive medical care or reach a hospital soon enough for the diagnosis, prescription and administration of a prescribed medicine before much of the irreversible damage from trauma has occurred. After an initial stroke, brain cells begin to die immediately and continue to die for several more hours, killed by a chemical chain reactions triggered by proteins that ooze from neighboring damaged cells. Research shows quickly cooling the brain will slow and prevent much of this damage by slowing these metabolic processes. Since brain cells are continuing to die following a stroke, lowering the stroke victim's body temperature lowers the temperature of the blood flowing to the victims brain, thereby lowering the temperature of the brain. Lowering body temperature immediately where the victim is located may in many cases be more important use of time than transport to a medical care or a hospital. Once thermal control has been initiated: the victim should be transported to medical care of a hospital as soon as possible. Even in an EMS vehicle, before the victim gets to medical care or to the hospital lowering body temperature has a prophylactic effect as this lowers the temperature of the brain, slowing, arresting, diminishing and/or mitigating subsequent consequential damages caused by the initial blood lot. Similar results are indicated for heart attack victims where a clot has landed in the heart and other infarctions such as those occurring in the spleen, liver and other vital organs. The portable thermal rescue/recovery system provides this immediate life-saving temperature reduction for a wide variety of medical emergencies.

The present invention, the portable thermal rescue/ recovery system (PTRRS), can be used as first aid for victims of hypothermia, stroke, heart attack, infraction, burns and other medical conditions body temperature control is needed. This system is suitable for use in land, sea and air rescue vehicles including Emergency Medical Service (EMS) vehicles which are used to recover and/or transport mammals, primarily humans, needing body temperature control. The volume of liquid needed for the PTRRS is ½ to ¾ of the weight of the mammal—or in the case of a human, not more than 100–150 lbs. Hence, the PORTABLE THERMAL RESCUE/RECOVERY SYSTEM is suitable for Coast Guard, Navy, law enforcement and other rescue helicopters and aircraft as well as land and water based rescue craft and vehicles of all sizes and in a personally portable mode, is suitable where the mammal cannot be quickly be moved to the rescue vehicle and immediate, in situ temperature control is indicated.

DETAILED DESCRIPTION OF THE INVENTION

Figure 1:
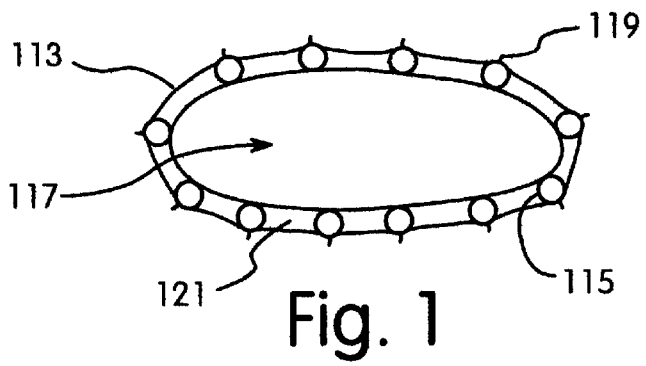
FIG. 1 is a cross sectional view of the mummy bag with a mammal in it.

The invention portable thermal rescue/recovery system includes a water-proof mummy bag in which a body or portion of a body of a mammal with hypothermia, stroke, burns or other condition which requires adjusting body temperature is placed. This system a cross-section of which is shown in FIG. 1 and a side view in FIG. 2, includes the mummy bag (222) with an external water-proof layer (113) with in which a series of inflatable bladders (115) running the length of the mummy bag along the body or portion of the body of the mammal (117) in the mummy bag. Once the mammal or portion of the mammal is placed in the mummy bag, each individual bladder is manually inflated a re-sealable stem tube (119) and a liquid of the desired temperature is added to the bag and fins the heat transfer channels (121) between the bladders. The liquid and inflated bladders suspend the mammal in a floating state, minimizing the points of and pressure on contacts between the mammal and supporting the mummy bag.

Figure 2:
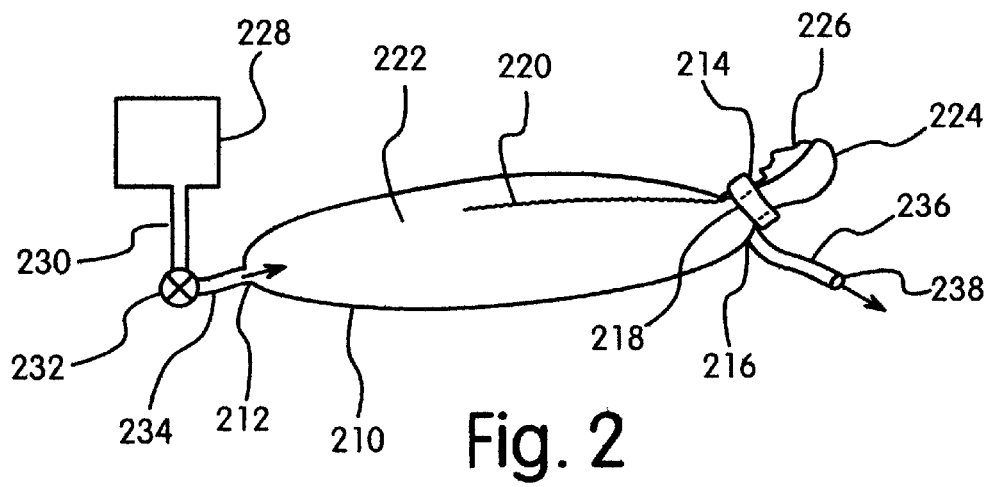
FIG. 2 is a side view of the mummy bag with source for a liquid and a discharge tube.

In FIG. 2, a side view of a simple portable thermal rescue/recovery system in which the liquid is allowed to flow around all surfaces of the of the body or portion of body of a mammal and then to a discharge drain (not shown). The mummy bag has a closed lower end (210) with a liquid inlet (212) and an open upper end (214) with a liquid outlet (216) and an u-shaped inflatable, double collar (218) with the zipper-like water-proof seam (220) from the open upper end, through the collar and along the upper surface of the mummy bag (222) allows for easy insertion and removal of the mammal (117). When the body of the mammal is placed in the mummy bag, a hood (224) is used over the head of the mammal so that thermal treatment is provided to the head (226) of the mammal (117). The liquid from a source (228) above the mummy bag (222) flows by gravity through a first tube (230) to a first valve (232) which is a one-way valve, through a second tube (234) to the liquid inlet (212) at the lower end (210) of the mummy bag. After the liquid flows around the body or portion of the body of the mammal in the mummy bag, the liquid exits through the liquid outlet (216), through a third tube (236) to a discharge point (238).

Figure 3:
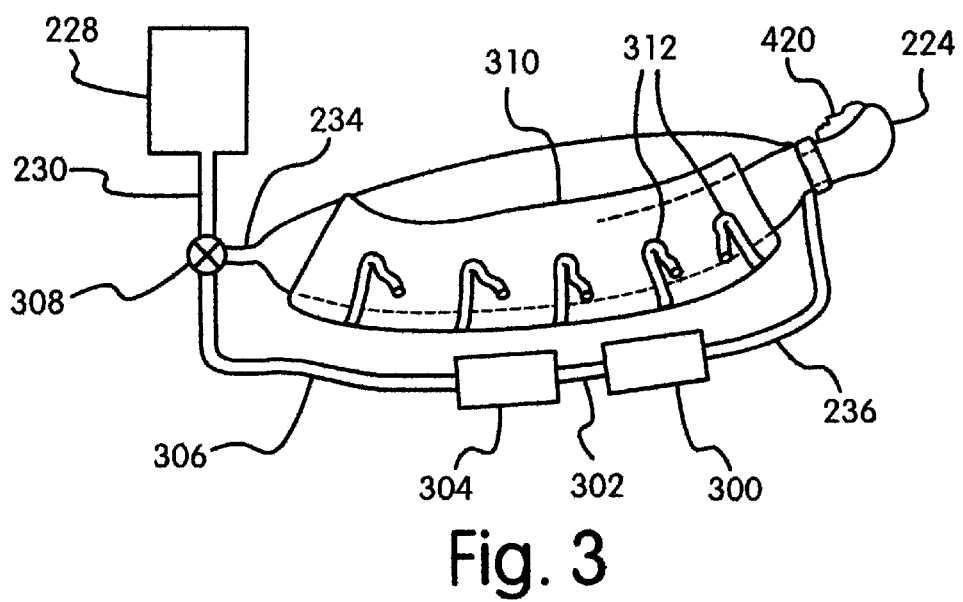
FIG. 3 is a side view of the mummy bag with a pump, heat exchanger, an external covering and straps.

In the preferred embodiment shown in FIG. 3, the discharge point (238) is connected to a pump (300) to a heat exchanger (304) by fourth tube (302) and then to second valve (308) which is a two-way valve. The liquid is transported from the lower end of the mummy bag to the upper end through the channels (121) along the body or portion of the body of the mammal where heat transfer between the mammal and liquid occurs. The liquid, after flowing along the mammal's body through the channels (121), is collected at the liquid outlet (216) at the upper end (214) and through the third tube (236), returned to the pump (300). The liquid is then transported by the pressure generated by the pump through a fifth tube (306) to a heat exchanger (304). The heat exchanger) adjusts the temperature of the liquid which by heat transfer increases or decreases the temperature of the body or portion of the body of the mammal (117) in the mummy bag (222).

A separate outer covering (310) of the mummy bag (222) having a plurality of circumferential straps (312), which after the bladders (115) and amount of liquid are set, is used to adjust the total volume of the combination of the mammal or the portion of the mammal and the liquid in the mummy bag, The covering and the straps, when adjusted control the amount of body weight which is supported by contact with the mummy bag and the rate of liquid flow along the body of the mammal. If necessary, the straps (312) can be adjusted to a point where the mammal or the portion of the mammal floats in the liquid, These straps allow the mummy bag to be adjusted to the various sizes of mammals, including humans, placed in the mummy bag. This covering and straps are strong enough to allow the mummy bag and mammal to be lifted by the straps and supported during relocations or transfers from one place to another such as from a rescue vehicle to a hospital gurney. The covering (310) is made of a tough, insulating material.

Due to the high heat capacity of the liquid in the system and for convenience of size and weight, the portable thermal rescue/recovery system uses as little as 12–18 gallons (100–150 lbs.) of the liquid. This volume of liquid and the pumping action is sufficient to fill operate and achieve rapidly the advantages of the portable thermal rescue/recovery system in controlling the temperature of the body or portion of the body of the mammal in the mummy bag.

For maximum heat transfer, the liquid is circulated at a rate faster than would normally be indicated if the purpose was to achieve a maximum change in the temperature of the liquid as is the case, for example, in an automobile radiator. The faster the liquid is circulated through the mummy bag, the lower the temperature difference between the liquid and the mammal can be and still achieve a high heat transfer rate. Even if the heat exchanger in the portable thermal rescue/recovery system were unavailable as in the case where the heat exchanger fails, it would still be better to circulate the liquid in the system than not, in order to maximize the transfer of heat between the liquid and the mammal until the temperature of the liquid and the mammal are identical.

Figure 4:
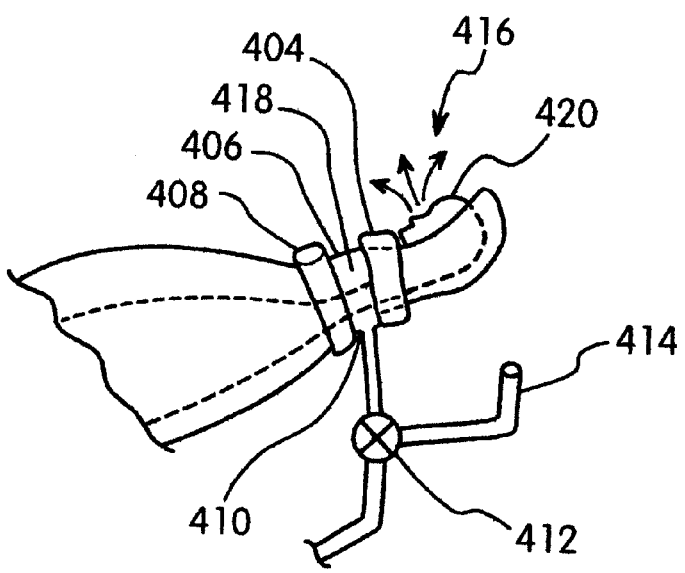
FIG. 4 shows details of the double collar, hood and bleed valve\medication port.

The thermal rescue/recovery system is gathered at the upper end of the body or portion of the body of the mammal with a U-shaped, inflatable double collar comprising an outer collar (404) and an inner collar (408) between which lies a small gap (406) sufficient for the exiting liquid to pool at the inlet (410) to third tube (236) and to be drawn into the third tube by action of the pump (300) as shown in FIG. 4. Some air is sucked in with the pooling liquid between the inner and outer collars. More air can be added to the liquid passing through the third tube (236) via the third valve (412), which is a one way valve, connected to a medication port (414), through which medicines and air can be added to the passing liquid. This air and liquid is pumped through the mummy bag with the air, exiting at the upper end (214) through the outlet at or near the temperature of the liquid. In cases where the body of a human has been inserted into the mummy bag, the U-shaped collars are inflated and then closed around the neck (418) by action of the water-proof seal (220), with the hood (224) enclosing the head (226) but not the face (420) as shown in FIG. 4. As this exiting air (416) is around the head of the human, it is breathed by the human providing additional thermal therapy in the air passages and lungs of the human.

Once the mammal has been placed in the mummy bag, warm (or cool) liquid is added from the external source (228) through the first tube (230), through the second valve (308), through the second tube (234) and into the mummy bag through the liquid inlet (212) as shown in FIG. 3. When the added liquid begins to pool at the inlet to the third tube (410) between the inner (408) and outer collars (404) at the upper end (214), the second valve (308) is switched, closing off the source and allowing the liquid along with some air to be transported by pressure generated by the pump (300) into the mummy bag.

Figure 5:
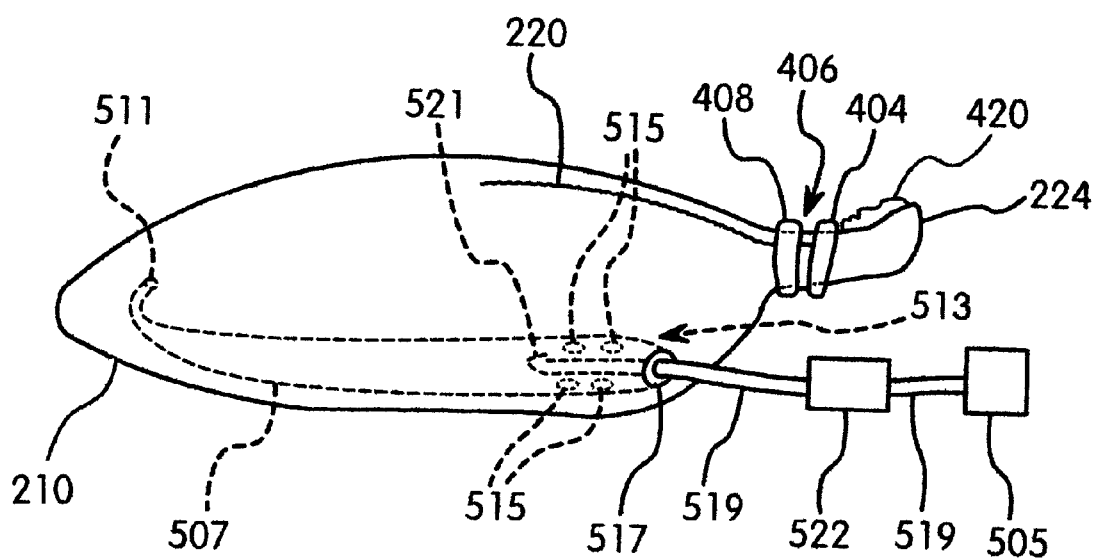
FIG. 5 shows a side view of the invention with a pressurized air source and heating source.

In applications involving rescue/recovery vehicles where the weight of the portable thermal rescue/recovery system is a concern as in a rescue helicopter, other aircraft surface effect craft or small boat (not shown), the pump (300) and heat exchanger (304) are eliminated by substituting a jet of air from a pressured air source (505) as shown in FIG. 5. This pressurized air is contained in a sixth tube (519) which runs from the air source (505), through a water-proof aperture (517) in the mummy bag (222) at the upper end (214) and to a nozzle (521) which is inserted into a seventh semi-rigid fabric tube (507). This seventh fabric tube is attached along a lower portion to the mummy bag and runs toward the lower end (210) of the mummy bag. This seventh semi-rigid fabric tube is attached to the mummy bag around the aperture (517), enclosing the sixth tube (519) from the pressurized air source (505) as it enters the mummy bag. This seventh tube has an outlet (511) at the lower end (210) of the mummy bag which is directed toward the upper end (214). This seventh tube (507) also has a series of small liquid inlet holes (515) between the nozzle (521) and the aperture (517). The pressurized air acts as a pumping system which is comprised of a sixth rigid tube (519) inserted in the aperture (517) into the semi-rigid fabric tube and a nozzle (521) which extends beyond the liquid inlet holes (515). As air in injected into the semi-rigid fabric tube, pressure is generate moving the liquid to the liquid outlet while drawing liquid through the inlet holes (515). This injected air is room temperature when cooling is needed or heated by a heat source (522), serving as both a pump and as a heating or cooling source for the liquid.

The liquid enters the seventh tube (519) through inlet holes (515) at the upper end of the mammal bag and exits at the lower end, flowing around the body or portion of the body of the mammal before eventually re-entering the inlet holes. The source (505) of the pressurized air can be a compressor, air pump of any kind, manual or powered, or; if available, the jet air can be drawn directly from a jet engine powering the rescue craft such a helicopter.

Whether a mechanical pump or air jet pump is used, a by-product of the pumping mechanism is either cool or warm moist air. As this air exits it follows the same path and has the same value as the air drawn into the third tube (236) with the liquid or the air bled in through the medical port (414).

For use with mammals suffering from burns cooling the liquid can be avoided if the initial liquid temperature is close to room temperature—70–75 degrees F.—without generating secondary medical issues such as convulsions which often accompany severe hypothermia. If the initial liquid temperature is about room temperature and the liquid used is limited to the weight of the mammal or less, then no additional cooling of the liquid is required if the mammal is transported to hospital following standard emergency procedures as indicated by the circumstances.

For all mammals requiring body temperature control whether all of the mammal's coverings or clothing is removed or not time is of the essence so that to avoid unnecessary delay only the most easily removed outer covering or clothing is removed. In burn cases, clothing is often burned onto the skin and removal of this burned clothing is difficult, time consuming and painful. An advantage of the portable thermal rescue/recovery system for burn victims is that treatment begins immediately when the liquid is added regardless of the presence of coverings or clothing. In such circumstances, removal of burned clothing is best left to doctors in the stable, controlled atmosphere of a hospital. After initial use of the PTRRS for a brief period of time, any additional layers of coverings or clothing on the mammal can be removed to allow continued heat transfer into or out of the mammal as indicated.

In applications where weight is not a major limitation as in ocean-going marine rescue craft and modern EMS vehicles, the volume of the liquid can be increased and the size of the supporting bladders reduced by under inflating them. If space and structure allow, the inflation of the bladders is limited and a larger volume of can be used, reducing or eliminating the portion of the mammal's weight which is supported by contact with the inflated bladders or mummy bag. This is of particular value in the case of burn victims where the skin may be stressed by supporting the weight of the mammal. Even in this application where weight is not an issue, the amount of liquid must limited to avoid the stresses from large motions and shifting gravitational and other force gradients generated by the motions of the rescue vehicle.

In circumstances where it is not practical or possible to bring the mammal to the portable thermal rescue,/recovery system, a compact, personally portable disposable portable thermal rescue/recovery system is used. In this compact, personally portable system, the tough outer cover and the straps are incorporated in the water-proof material comprising the mummy bag. This compact, personally portable system is carried in a deflated, folded mode in a small pack (not shown) to the mammal along with a separate container of the liquid of the appropriate temperature. In this case, the bladders are inflated once the mummy bag has been placed around the mammal. Then, 20-to-40 lbs. of pre-heated, room-temperature or pre-cooled liquid from the separate container is added to the inflated mummy bag around the mammal, the seal (220) is closed and the straps (312) are adjusted. Circulation is accomplished by manually flushing the liquid back and forth through the heat transfer channels (121) along the body of the mammal until movement of the mammal to a rescue vehicle with a complete thermal rescue system is possible.

In the personally portable system and in applications in rescue vehicles where a heating or cooling source is not available such as in a temporary installation in a rescue vehicle where the PTRRS has not been connected to the vehicle's heating, cooling and power systems, for mammals needing increased body temperature, the liquid is heated by the catalytic release of an exothermal reaction by a combination of suitable chemicals or a chemical having properties similar to liquid sodium acetate which rises from room temperature to about 137 degrees F. when stimulated by a singularity such as a mechanical tap or by X internally mounted metal clicker disk as used in small hand held pocket warmers. Packets of these chemicals are carried with the personally portable system and once the exothermic reaction has been initiated, these packets are inserted into the mummy bag through the seal (220) along the upper side. For mammals needing decreased body temperature, a room temperature liquid is used and replaced when additional or continued cooling is indicated.

Finally, in applications where weight is not critical and/or where it is desired or medically necessary to keep the body or portion of the body of the mammal (117) from being immersed in the liquid, the body or portion of the body of the mammal is placed in a thin water-proof liner (not shown) before being inserted into the portable thermal rescue/recovery system. In this application, the volume of liquid is increased and the inflation of the bladders (115) is limited to allow the body or portion of the body of the mammal to float or nearly float in the liquid so as to remain in continuous contact with the circulating liquid and minimize the stress on the mammal's skin caused by its having to support the weight of the mammal.

LIST OF PARTS NUMBERS
In connection with the figures, the following list of the names of the parts of the instant invention are noted:

| | |
|---|---|
| 111. | Mummy bag; |
| 113. | External water-proof layer; |
| 115. | Inflatable bladders; |
| 117. | Body or portion of the body; |
| 119. | Stem tube; |
| 121. | Channels; |
| 210. | Closed lower end; |
| 212. | Liquid inlet; |
| 214. | Open upper end; |
| 216. | Liquid outlet; |
| 218. | U-shaped double collar; |
| 220. | Re-sealable, water-proof seam; |
| 222. | Mummy bag; |
| 224. | Hood; |
| 226. | Head; |
| 228. | Source; |
| 230. | First tube; |
| 232. | First one way valve; |
| 234. | Second tube; |
| 236. | Third tube; |
| 238. | Discharge point; |
| 300. | Connected to a pump |
| 302. | Fourth tube |
| 304. | Heat exchanger |
| 306. | Fifth tube |
| 308. | Second valve |
| 310. | Outer covering; |
| 312. | Straps; |
| 404. | Outer collar; |
| 406. | Small gap; |
| 408. | Inner collar; |
| 410. | Third tube inlet; |
| 412. | Third valve; |
| 414. | Medication port; |
| 418. | Neck; |
| 416. | Exiting air; |
| 420. | Face; |
| 507. | Seventh semi-rigid fabric tube; |
| 515. | Liquid inlet holes; |
| 517. | Aperture; |
| 519. | Sixth tube; |
| 521. | Nozzle; |
| 522. | Heat source. |

What is claimed is:

1. A portable system for rapidly changing and controlling the temperature of body, limb, head or other portion of the body of a mammal using energy transfer between a liquid which is water or other aqueous liquid and skin of the mammal, by direct liquid-to-skin contact, comprising:

(a) a mummy bag, sized to conform to shape of the body or the portion of the body of the mammal, having an upper end with an adjustable opening, a closed lower end and made of at least one layer of a water-proof materials with a liquid inlet at the lower end and upper end having a liquid outlet;

(b) a water-proof seam on upper surface of the water-proof material of the which can be unsealed and then resealed, providing an opening sufficiently large to allow insertion into the mummy bag of the body or the portion of the body of the mammal whose temperature is to be controlled;

(c) along the sides of the mummy bag, imbedded in the water-proof materials, a series of inflatable bladders running from the lower end to the upper end of the mummy bag along the body or the portion of the body of the mammal which can be inflated to improve the conformance of the mummy bag to the shape of the body or the portion of the body of the mammal whose temperature is controlled while at the same time providing channels for the liquid to flow between the bladders and along the skin of the mammal;

(d) means for transporting the liquid, to and into the lower end of the mummy bag through the liquid inlet from a supply of the liquid;

(e) means for transporting the liquid in the mummy bag through the liquid outlet which is located at the upper end of the mummy bag between two collars which can be adjusted independently by inflatable bladders or straps to conform to the neck of the body of the mammal or the upper most part of the portion of the body of the mammal, to a storage container, to a drain or to a discharge point; and (f) a separate outer covering of the mummy bag made of a tough insulating fabric material, having a plurality of circumferential straps which serve as lifting points when the mammal bag is moved and which after the bladders and amount of liquid are set, are used to adjust the total volume of the combination of the mammal or the portion of the mammal and the liquid in the mummy bag to surround the body or portion of the body of the mammal in the liquid so as float the mammal or the portion of the mammal, controlling the amount of body weight which is supported by contact with the mummy bag and the rate of liquid flow along the body of the mammal.

2. The system for rapid temperature control according to claim 1, wherein the means for transporting the liquid is pressure generated by a pump or by hydrostatic pressure due to gravity.

3. The system for rapid temperature control according to claim 1, wherein the liquid is transported by pressure generated by a pump from a source to and into the mummy bag by action of a two way valve between the pump and the source, wherein the valve is activated when sufficient liquid has been transported to and into the mummy bag that the liquid flows from the upper liquid outlet so that continued operation of the pump after the valve to the source is closed transports the liquid in the mummy bag from the liquid outlet at the upper end to and through the pump and from the pump to and into the lower end of the mummy bag.

4. The system for rapid temperature control according to claim 3 further includes a means for controlling the temperature of the recirculating liquid which includes a heat exchanger to which the pressure generated by the pump transports the liquid to pass through the heat exchanger before the liquid is further transported to and into the liquid inlet at the lower end of the mummy bag, and which further includes a thermometer, a source of heat selected from the group consisting of (i) an engine, (ii) a generator engine, (iii) an auxiliary engine, (iv) a heat source provided by fuel, (x) a heat source provided by a heat pump, (vi) a heat source provided by solar energy, (vii) a heat source from exothermic chemical reactions including the crystallization of liquid sodium acetate and (viii) a heat source provided by electricity, or which further includes a heat sink selected from the group consisting of (i) a refrigerator, (ii) a refrigerant: (iii) an air cooled radiator, (iv) a liquid cooled radiator, (v) a pool of previously cooled materials selected from a group consisting of (a) ice, (b) iced liquids, (c) dry ice, (d) a cold plate, which further includes a means of controlling the amount of thermal energy add to or taken from the recirculating liquid.

5. The system for rapid temperature control according to claim 4 further includes a medicine port comprised of a second one way valve between the liquid outlet at the upper end of the mummy bag and the intake of the pump connected to a tube through which medicines and other substances may be introduced into the liquid as it is pumped into the mummy bag and around the body or the portion of the body of the mammal whose body temperature is being controlled.

6. The system for rapid temperature control according to claim 5, wherein the pumping action which moves the liquid around the body or the portion of the body of the mammal is provided by a stream of pressurized air injected into the liquid from a source selected from the group which includes (a) air bled from a jet engine, (b) a compressor, (c) a manual air bellows, and wherein the temperature of the liquid is controlled by the temperature of the injected air which is heated or cooled by passage through a heat exchanger before being injected into the liquid.

7. The system for rapid temperature control according to claim 5, wherein a the body or the portion of the body of the mammal to be enclosed in the mummy bag is first place in a thin plastic liner.

8. The system for rapid temperature control according to claim 1, wherein the bag like container and a portable source of the liquid is taken to the mammal for immediate, emergency service, the source of the liquid includes a separate container wherein the temperature of the liquid has been adjusted to an initial desired level which is either warmer or cooler than body-temperature of the mammal and the liquid is introduced into the bag structure through the collars at the upper end of the mummy bag, providing immediate temperature change.

9. The system for rapid temperature control according to claim 8 wherein heat is added to the liquid by packets of chemicals imbedded between the bladders which can be caused to initiate exothermic reactions such as the crystallization of liquid sodium acetate.

10. A personally portable system for rapidly changing and controlling the temperature of the body, a limb, the head or other portion of the body of a mammal using energy transfer between a liquid which includes water or another aqueous liquid and the skin of the mammal, by direct liquid-to-skin contact including:

(a) a disposable mummy bag sized to conform to the shape of the body or the portion of the body of the mammal having an upper end with an adjustable opening, a closed lower end with a drain and made of a layer of a water-proof materials;

(b) a plastic container which can be sealed and unsealed for transporting to the mammal the liquid which has been adjusted to the desired temperature with a means to pour the liquid into the bag structure through the adjustable opening;

(c) a water-proof seam on the upper surface of the water-proof material of the mummy bag which can be unsealed and then resealed, providing an opening sufficiently large to allow easy insertion into the mummy bag of the body or a portion of the body of the mammal whose temperature is to be controlled;

(d) along the sides of the mummy bag, imbedded in the water-proof materials, a series of inflatable bladders running from the lower end to the upper end of the mummy bag along the body or the portion of the body of the mammal, which can be inflated to improve the conformance of the mummy bag to the shape of the body or the portion of the body of the mammal whose temperature is controlled while at the same time providing channels for the liquid to flow between the bladders and along the skin of the mammal;

(e) means for manually generating pressure to transport the liquid from one end to the other end of the mummy bag selected from a group including, (i) a hand pump, (ii) a foot pump, (iii) a bellows, or (iv) a tube into which air is blown;

(f) means at the lower end of the mummy bag to open the drain, allowing gravity pressure to empty the bag structure and to close the drain before additional liquids of the desired temperature are introduced at the upper end;

(g) a separate outer coveting of the mummy bag made of a thin water-proof insulating material having at least three circumferential straps which after the bladders and amount of liquid are set, are used to adjust the total volume of the combination of the mammal or the portion of the mammal and the liquid in the bag structure to achieve the desired level of flotation, the desired amount of body weight which is supported by contact with the mummy bag and the desired rate of liquid flow along the body of the mammal.

11. The system for rapid temperature control according to claim 10 wherein heat is added to the liquid by packets of chemicals imbedded between the bladders which can be caused to initiate exothermic reactions such as the crystallization of liquid sodium acetate.

* * * * *